(12) United States Patent
Weber et al.

(10) Patent No.: US 9,320,628 B2
(45) Date of Patent: Apr. 26, 2016

(54) ENDOPROSTHESIS DEVICES INCLUDING BIOSTABLE AND BIOABSORABLE REGIONS

(71) Applicant: Boston Scientific Scimed, Inc., Maple Grove, MN (US)

(72) Inventors: Jan Weber, Maastricht (NL); James M. Anderson, Fridley, MN (US); Derek C. Sutermeister, Ham Lake, MN (US); Cass Alexander Hanson, St. Paul, MN (US); Timothy A. Ostroot, Cokato, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

(21) Appl. No.: 14/479,912

(22) Filed: Sep. 8, 2014

(65) Prior Publication Data

US 2015/0073522 A1    Mar. 12, 2015

Related U.S. Application Data

(60) Provisional application No. 61/875,370, filed on Sep. 9, 2013.

(51) Int. Cl.
| | |
|---|---|
| *A61F 2/06* | (2013.01) |
| *A61F 2/91* | (2013.01) |
| *A61F 2/915* | (2013.01) |
| *A61F 2/856* | (2013.01) |
| *A61F 2/82* | (2013.01) |

(52) U.S. Cl.
CPC .............. *A61F 2/915* (2013.01); *A61F 2/856* (2013.01); *A61F 2002/061* (2013.01); *A61F 2002/825* (2013.01); *A61F 2002/91541* (2013.01); *A61F 2002/91575* (2013.01); *A61F 2250/0018* (2013.01); *A61F 2250/0029* (2013.01); *A61F 2250/0031* (2013.01); *A61F 2250/0036* (2013.01); *A61F 2250/0039* (2013.01)

(58) Field of Classification Search
CPC ...... A61F 2/06; A61F 2210/0004; A61F 2/82
USPC ................................. 623/1.15–1.31
See application file for complete search history.

(56) References Cited

U.S. PATENT DOCUMENTS

| | | | | |
|---|---|---|---|---|
| 5,827,321 | A * | 10/1998 | Roubin | A61F 2/91 606/195 |
| 6,264,690 | B1 * | 7/2001 | Von Oepen | A61F 2/82 623/1.15 |
| 6,325,825 | B1 * | 12/2001 | Kula | A61F 2/91 623/1.15 |
| 6,663,664 | B1 | 12/2003 | Pacetti | |
| 7,455,688 | B2 * | 11/2008 | Furst | A61F 2/82 623/1.31 |
| 7,594,928 | B2 | 9/2009 | Headley, Jr. et al. | |
| 7,722,578 | B2 * | 5/2010 | Arney | A61M 25/0009 604/264 |
| 7,862,607 | B2 | 1/2011 | McDermott et al. | |

(Continued)

*Primary Examiner* — Suzette J Gherbi
(74) *Attorney, Agent, or Firm* — Seager, Tufte & Wickhem, LLP

(57) ABSTRACT

Some embodiments are directed to medical devices, and methods for making and using the medical devices. An exemplary endoprosthesis includes an expandable tubular framework having a proximal end, a distal end, and a lumen extending therethrough. The tubular framework includes a number of interconnected biostable struts. The tubular framework has a proximal region extending distally from the proximal end to an intermediate location, and a distal region extending proximally from the distal end to the intermediate location. The distal region of the tubular framework is more flexible than the proximal region.

17 Claims, 15 Drawing Sheets

(56) References Cited

U.S. PATENT DOCUMENTS

| | | |
|---|---|---|
| 8,128,689 B2 | 3/2012 | Weber et al. |
| 8,500,797 B2 * | 8/2013 | Olson ............... A61M 25/0009 623/1.42 |
| 2001/0021873 A1 * | 9/2001 | Stinson ............ A61B 17/12022 623/1.34 |
| 2004/0098119 A1 * | 5/2004 | Wang ...................... A61F 2/82 623/1.42 |
| 2005/0010279 A1 | 1/2005 | Tenerz et al. |
| 2005/0033399 A1 | 2/2005 | Richter |
| 2005/0222671 A1 | 10/2005 | Schaeffer et al. |
| 2006/0122694 A1 | 6/2006 | Stinson et al. |
| 2006/0129222 A1 | 6/2006 | Stinson |
| 2007/0219626 A1 | 9/2007 | Rolando et al. |
| 2007/0219642 A1 | 9/2007 | Richter |
| 2008/0069858 A1 | 3/2008 | Weber |
| 2009/0012599 A1 | 1/2009 | Broome et al. |
| 2009/0062905 A1 | 3/2009 | Moore, Jr. et al. |
| 2009/0192588 A1 | 7/2009 | Shin et al. |
| 2009/0306755 A1 * | 12/2009 | Dickinson ................ A61F 2/07 623/1.3 |
| 2009/0306756 A1 | 12/2009 | Cho et al. |
| 2009/0306765 A1 | 12/2009 | Weber |
| 2009/0306766 A1 | 12/2009 | McDermott et al. |
| 2010/0030326 A1 | 2/2010 | Radhakrishnan et al. |
| 2010/0109204 A1 * | 5/2010 | Wu ........................ B29C 59/00 264/446 |
| 2010/0125328 A1 | 5/2010 | Flanagan |
| 2011/0238154 A1 * | 9/2011 | Murphy ......... A61B 17/320725 623/1.15 |
| 2013/0173016 A1 * | 7/2013 | Devereux .................. A61F 2/88 623/23.66 |

* cited by examiner

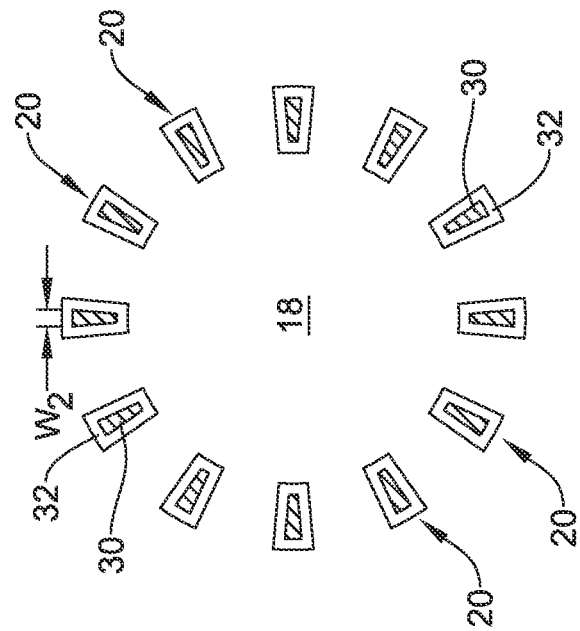
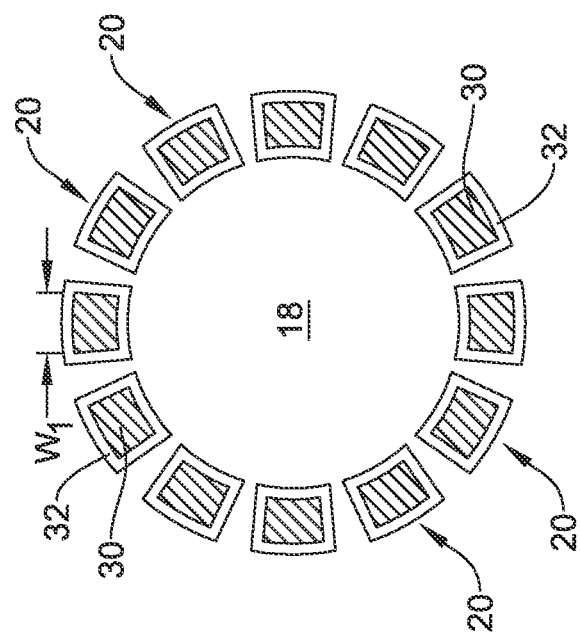
Figure 4A
Figure 4B

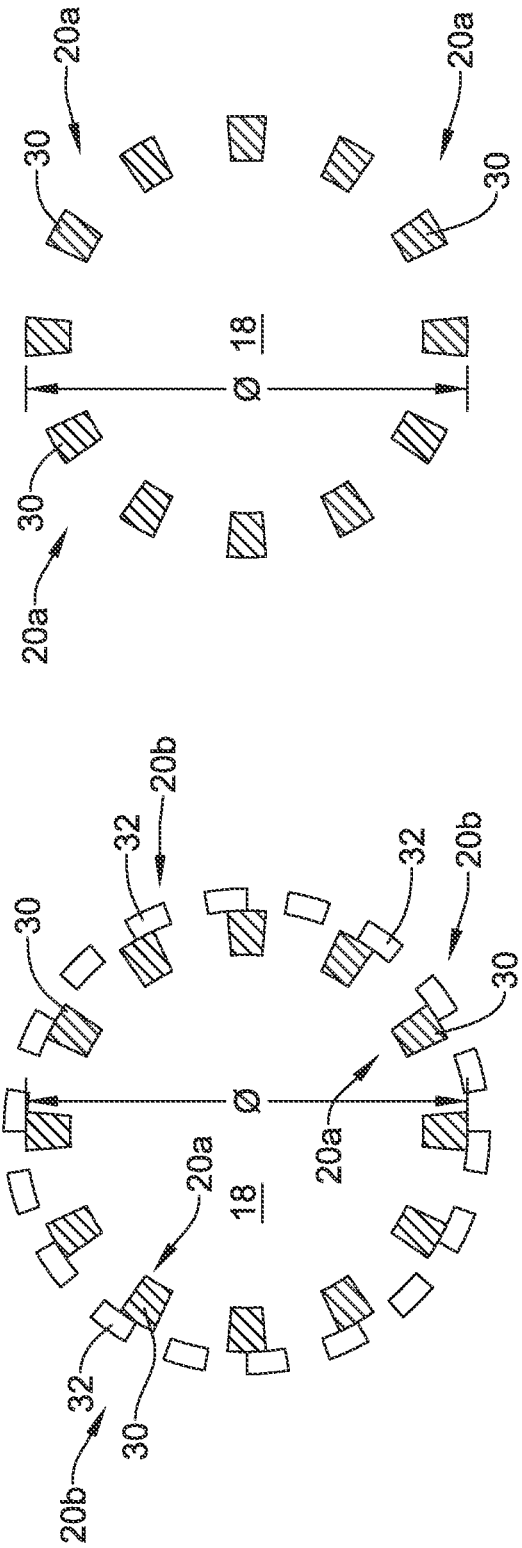

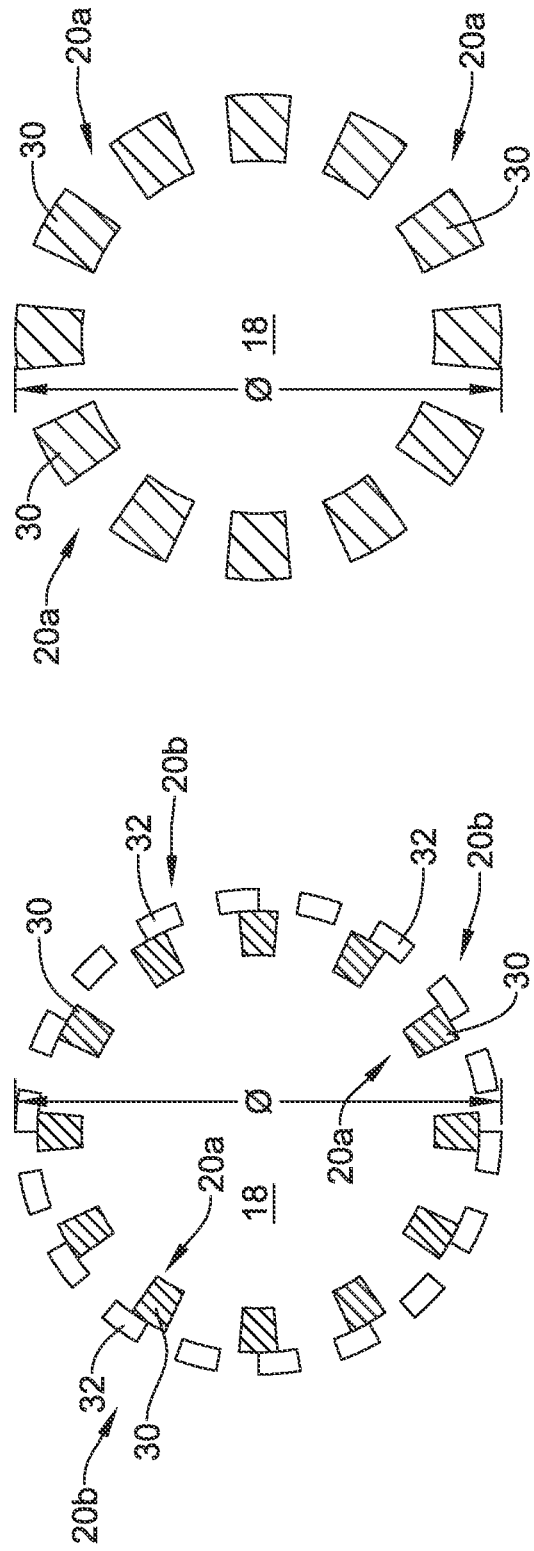

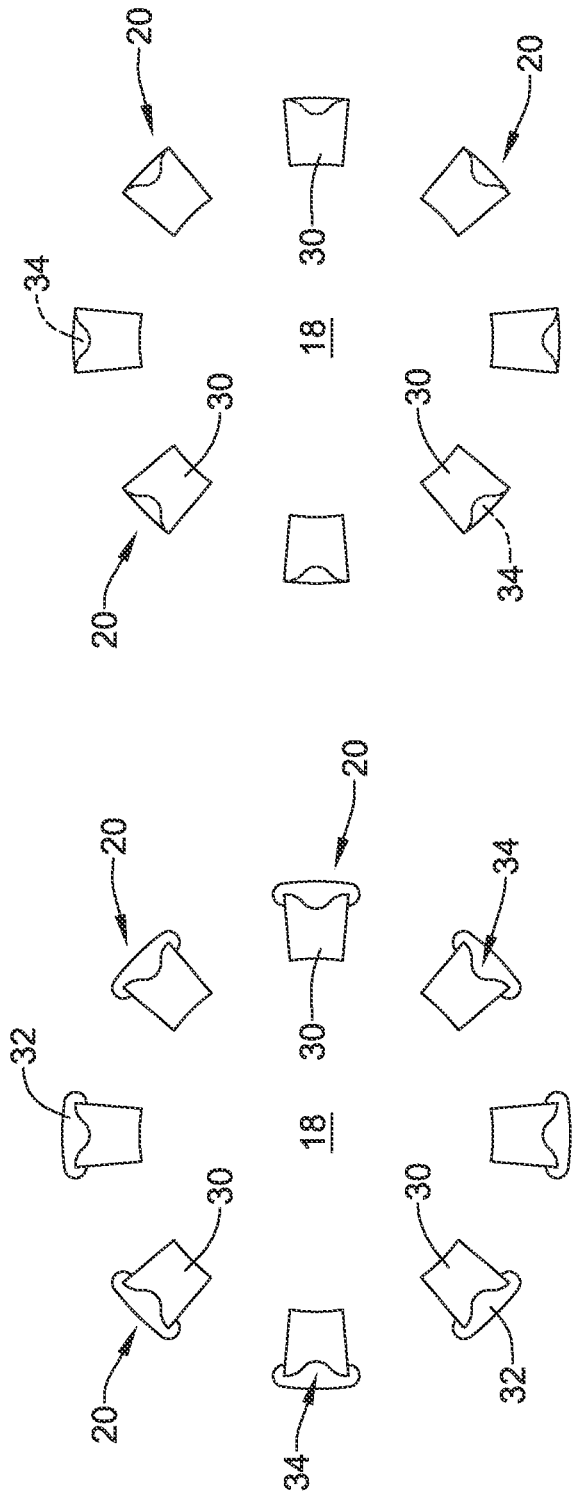

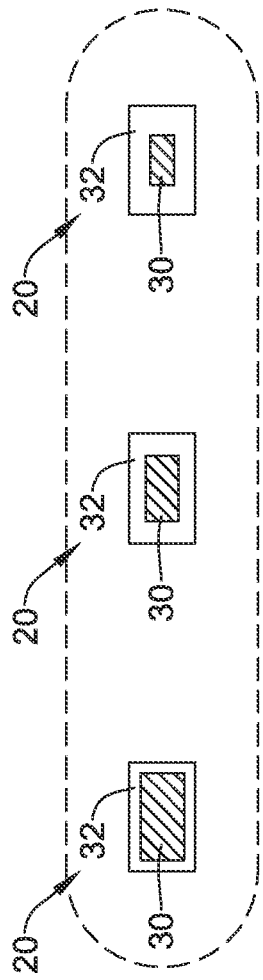
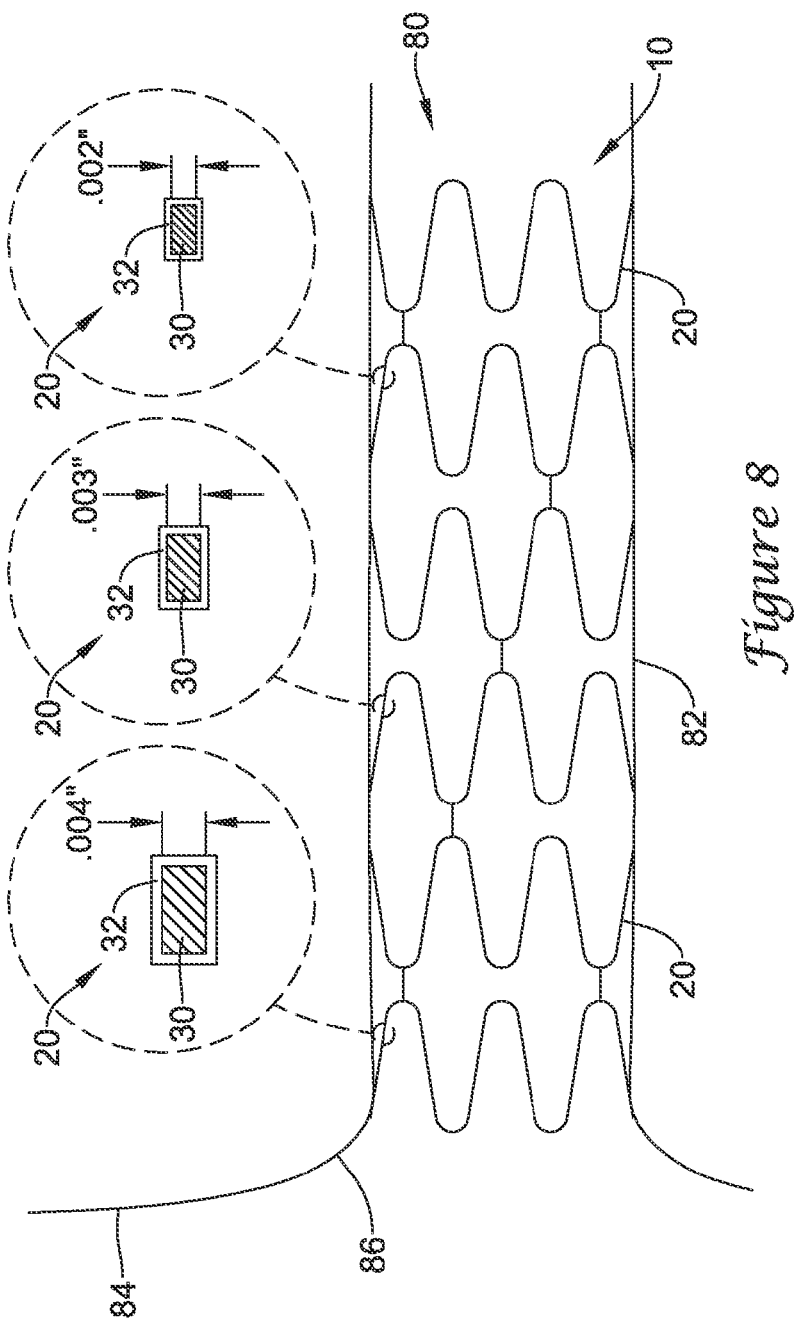

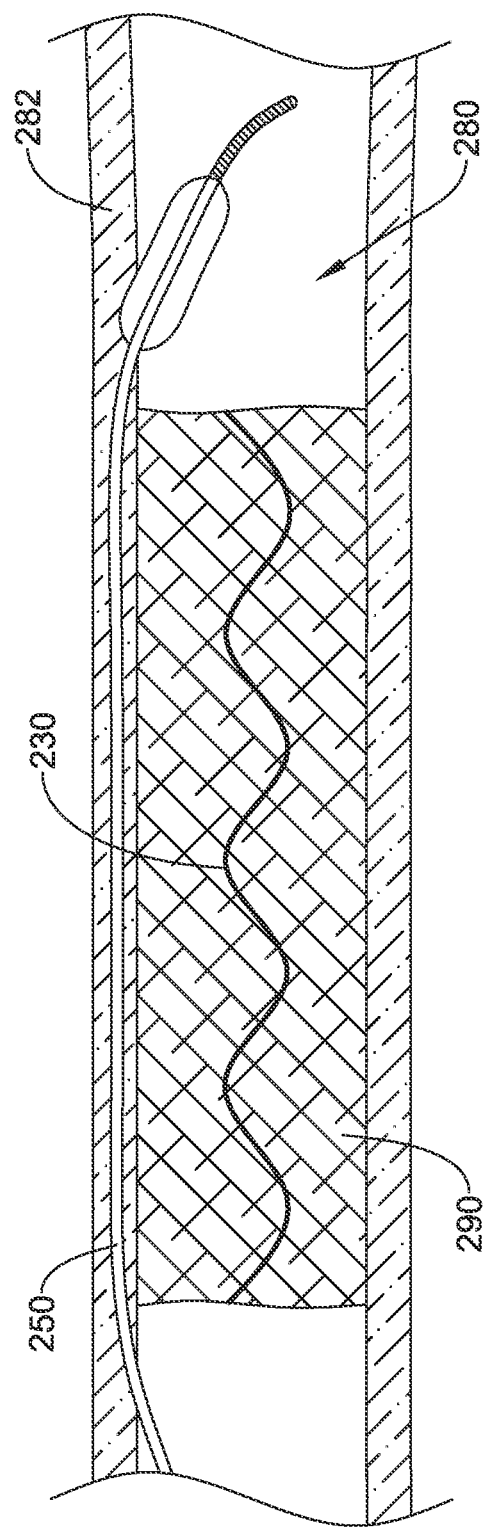

ENDOPROSTHESIS DEVICES INCLUDING BIOSTABLE AND BIOABSORABLE REGIONS

CROSS-REFERENCE TO RELATED APPLICATIONS

This application claims priority under 35 U.S.C. §119 to U.S. Provisional Application Ser. No. 61/875,370, filed Sep. 9, 2013, the entirety of which is incorporated herein by reference.

TECHNICAL FIELD

Some embodiments relate to medical devices, such as endoprostheses, and methods for manufacturing and using the medical devices. For example, endoprostheses including bioabsorbable portions and biostable portions are disclosed.

BACKGROUND

The body includes various passageways including blood vessels, such as arteries, urinary, biliary, tracheobronchial, esophageal or renal tracts, and other body lumens. These passageways sometimes become occluded or weakened, or otherwise structural support may be desired. For example, they can be occluded by a tumor, restricted by plaque, or weakened by an aneurysm. When this occurs, the passageway can be reopened or reinforced, or even replaced, with a medical endoprosthesis. The endoprosthesis may be implanted in a passageway or lumen in the body. Many endoprostheses are tubular members, examples of which include stents, stent grafts, covered stents, aortic valves, etc.

Some endoprostheses are made from fully bioabsorbable materials which will gradually dissolve or be absorbed by the body over a period of time after implantation. Other endoprostheses are made from biostable materials, such as biostable metallic materials and/or polymeric materials which will remain in the body lumen indefinitely after implantation.

The endoprosthesis should exhibit sufficient strength to retain the endoprosthesis at the desired location within the anatomy. For instance, regarding stents configured to be placed proximate an aortic ostium, it may be desirable to configure the stent to have a proximal region positioned proximate the aortic ostium that is stronger than a distal region of the stent extending into the coronary artery away from the aortic ostium due, at least in part, to the larger forces involved and the larger diameter of the vessel on the ostium side. However, it may be desirable to maintain flexibility along other portions of the stent. In other applications, such as in the tortuous vasculature, it may be desirable to utilize a stent that provides sufficient initial stability to the vessel, but over time restores vasomotion in the stented vessel.

Accordingly, it may be beneficial to provide alternative endoprostheses as well as methods for manufacturing and using the alternative endoprostheses that provide sufficient structural support while maintaining a desired flexibility. Some embodiments are therefore directed to several alternative designs of endoprosthesis structures and assemblies, as well as methods of making and using the alternative endoprosthesis structures and assemblies.

SUMMARY

One illustrative embodiment includes an endoprosthesis having an expandable tubular framework. The tubular framework has a proximal end, a distal end, and a lumen extending therethrough. The tubular framework includes a number of interconnected biostable struts. A proximal region of the tubular framework extends distally from the proximal end to an intermediate location, and a distal region of the tubular framework extends proximally from the distal end to the intermediate location. The distal region of the expandable tubular framework is more flexible than the proximal region.

Another embodiment of an endoprosthesis includes an expandable tubular framework. The tubular framework has a first end, a second end, and a lumen extending therethrough. The tubular framework includes a number of interconnected bioabsorbable struts. At least one biostable wire extends generally longitudinally along the tubular framework. The biostable wire is configured to provide longitudinal support to a vessel wall after the tubular framework is absorbed.

Yet another illustrative embodiment includes a method of implanting an endoprosthesis that has an expandable tubular framework in a coronary artery proximate to an aortic ostium. The tubular framework has a proximal end, a distal end, and a lumen extending therethrough. The tubular framework includes a number of interconnected biostable struts, and a bioabsorbable material disposed on a portion of the interconnected biostable struts. The endoprosthesis is positioned in the coronary artery with the proximal end proximate to the aortic ostium. The method also includes expanding the tubular framework to exert a radially outward force against the coronary artery. A proximal region of the endoprosthesis proximate to the proximal end has an initial stiffness if expanded that is greater than an initial stiffness of a distal region of the endoprosthesis. The proximal region is configured to have a reduced stiffness that is less than the initial stiffness over a period of time as the bioabsorbable material is absorbed. The above summary of some embodiments is not intended to describe each disclosed embodiment or every implementation of the present disclosure. The Figures, and Detailed Description, which follow, more particularly exemplify these embodiments, but are also intended as exemplary and not limiting.

BRIEF DESCRIPTION OF THE DRAWINGS

The disclosure may be more completely understood in consideration of the following detailed description of various embodiments in connection with the accompanying drawings, in which:

FIGS. 4A and 4B are alternative cross-sectional views taken along lines A-A and B-B of FIG. 1, respectively, in which the width of the proximal struts is greater than the width of the distal struts, and a bioabsorbable material is disposed at or on the biostable struts;

FIGS. 5A and 5B are alternative cross-sectional views taken along lines A-A and B-B of FIG. 1, respectively, in which the proximal region of the endoprosthesis includes a bioabsorbable expandable framework disposed at or on a biostable expandable framework;

FIGS. 6A and 6B are alternative cross-sectional views taken along lines A-A and B-B of FIG. 1, respectively, in which the proximal region of the endoprosthesis includes a bioabsorbable expandable framework disposed at or on a biostable expandable framework;

FIGS. 7A and 7B are alternative cross-sectional views taken along lines A-A and B-B of FIG. 1, respectively, in which the proximal region of the endoprosthesis includes a bioabsorbable material disposed in a channel of the biostable struts;

FIG. 8 is a cross-sectional view illustrating placement of an exemplary endoprosthesis at the aorta ostium, the illustrative endoprosthesis including a biostable expandable framework having a varying thickness along its length and a bioabsorbable material disposed on the biostable struts;

FIG. 8A are alternative cross-sectional views of the endoprosthesis of FIG. 8;

FIGS. 12A-12B illustrate advantages of the biostable wire of the endoprosthesis of FIG. 10.

DETAILED DESCRIPTION

Definitions of certain terms are provided below and shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same or substantially the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a," "an," and "the" include or otherwise refer to singular as well as plural referents, unless the content clearly dictates otherwise. As used in this specification and the appended claims, the term "or" is generally employed to include "and/or," unless the content clearly dictates otherwise.

The following detailed description should be read with reference to the drawings, in which similar elements in different drawings are identified with the same reference numbers. The drawings, which are not necessarily to scale, depict illustrative embodiments and are not intended to limit the scope of the disclosure.

Figure 1:
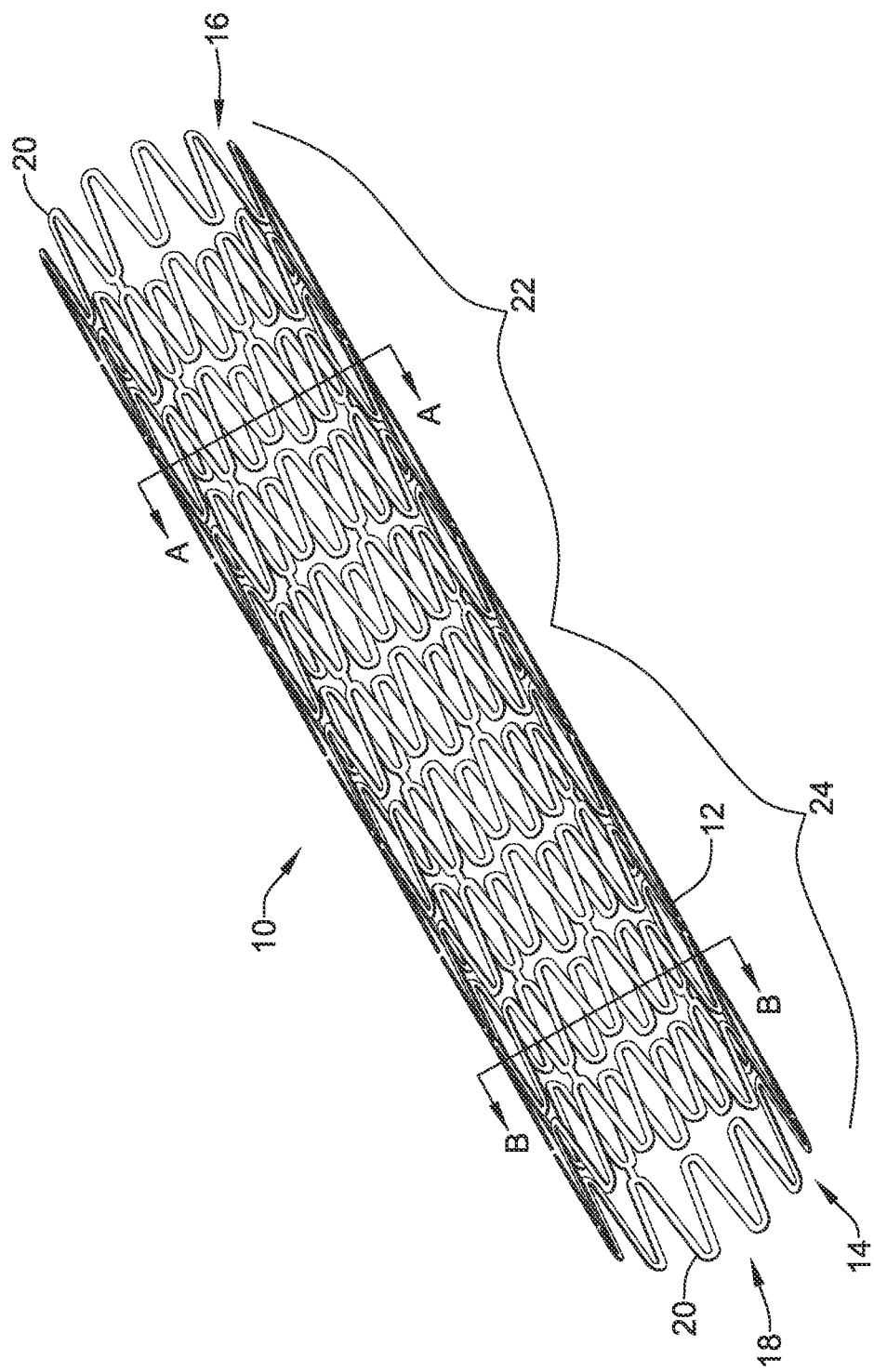
FIG. 1 is a perspective view of an exemplary endoprosthesis.

FIG. 1 illustrates an exemplary endoprosthesis 10. The endoprosthesis 10 may be configured to be positioned in a body lumen for a variety of medical applications. For example, the endoprosthesis 10 may be used to treat a stenosis in a blood vessel, used to maintain a fluid opening or pathway in the vascular, urinary, biliary, tracheobronchial, esophageal or renal tracts, or position a device such as an artificial valve or filter within a body lumen, in some instances. In some instances, the endoprosthesis 10 may be a prosthetic graft, a stent-graft, or a stent (e.g., a vascular stent, tracheal stent, bronchial stent, esophageal stent, etc.), an aortic valve, filter, etc. Although illustrated as a stent, the endoprosthesis 10 may be any of a number of devices that may be introduced endoscopically, subcutaneously, percutaneously or surgically to be positioned within an organ, tissue, or lumen, such as a heart, artery, vein, urethra, esophagus, trachea, bronchus, bile duct, or the like.

The endoprosthesis 10 may include a proximal end 16, a distal end 14, and an expandable tubular framework 12 disposed about a longitudinal axis of the endoprosthesis 10 that defines a lumen 18 extending therethrough. The term 'expandable tubular framework 12' may be referred to as 'expandable framework 12' hereafter. The expandable framework 12 may include a number of interconnected struts 20 to form a mesh-like structure of the expandable framework 12. The struts 20 may be configured to transition from a compressed state to an expanded state.

The expandable framework 12 may include a proximal region 22 and a distal region 24, which are separated by an intermediate location. The proximal region 22 includes the proximal end 16 and extends distally therefrom to the intermediate location. The distal region 24 extends distally from the intermediate location to the distal end 14. In other words, the distal region 24 extends proximally from the distal end 14 to the intermediate location. The intermediate location can be or otherwise define a midpoint in the direction of elongation of the expandable framework 12, such that the proximal and distal regions 22, 24 have the same lengths. Alternatively, the intermediate location can be disposed at a location other than the midpoint, such that the proximal and distal regions 22, 24 have different lengths.

The endoprosthesis 10 may be configured to be implanted in the vasculature of a patient, such as an aortic ostium, tortuous vessels, etc. In other embodiments, the endoprosthesis 10 may be configured to be implanted in the urinary, biliary, tracheobronchial, esophageal or renal tracts, for example. Since the endoprosthesis 10, or a portion thereof, may be intended to be implanted permanently in the body lumen, the endoprosthesis 10 may be made, at least in part, from a biostable material. Examples of the biostable metal materials may include, but are not limited to, stainless steel, tantalum, tungsten, niobium, platinum, nickel-chromium alloys, cobalt-chromium alloys such as Elgiloy® and Phynox®, nitinol (e.g., 55% nickel, 45% titanium), and other alloys based on titanium, including nickel titanium alloys, or other suitable metals, or combinations or alloys thereof. Some suitable biostable polymeric materials include, but are not necessarily limited to, polyamide, polyether block amide, polyethylene, polyethylene terephthalate, polypropylene, polyvinylchloride, polyurethane, polytetrafluoroethylene, polysulfone, and copolymers, blends, mixtures or combinations thereof.

Further, the struts 20 of the proximal region 22 may be coated with a bioabsorbable material or otherwise include a bioabsorbable material, thereby increasing the initial strength of the proximal region 22, such as by increasing the width, thickness, configuration, or other property of the proximal region 22. This coating may increase thickness of the struts 20 of the proximal region 22, thereby providing more stiffness to the proximal region 22. Such structure may be used, for example, in an aortic ostium, where larger forces are required and diameter of the vessel on the ostium side of the aortic ostium is larger.

Examples of suitable bioabsorbable materials may include polymers, such as poly-L-lactide (PLLA), polyglycolide (PGA), polylactide (PLA), poly-D-lactide (PDLA), polycaprolactone, polydioxanone, polygluconate, polylactic acid-polyethylene oxide copolymers, modified cellulose, collagen, poly(hydroxybutyrate), polyanhydride, polyphosphoester, poly(amino acids), and combinations thereof. The bioabsorbable material may be disposed at or on the proximal region 22 in different configurations. Some different embodiments of such configurations will be discussed in detail in conjunction with subsequent figures.

In some embodiments, the struts 20 of the endoprosthesis 10 may be arranged in suitable pattern, such as a serpentine configuration, a mesh, a fenestrated pattern, or other arrangement. For example, a number of the struts 20 can form a number of alternating peaks and troughs. The struts 20 may have an outer surface and an inner surface. In some embodiments, the outer surface is the abluminal surface of the endoprosthesis 10, and the inner surface is the luminal surface of the endoprosthesis 10. A thickness of the struts 20 may be measured between the outer surface and the inner surface in a radial direction from the central longitudinal axis of the endoprosthesis 10. A width of the struts 20 may be measured perpendicular to the thickness between side surfaces of the struts 20. Each of the struts 20 of the expandable framework 12 has a width W, and a thickness T.

Figure 2B:
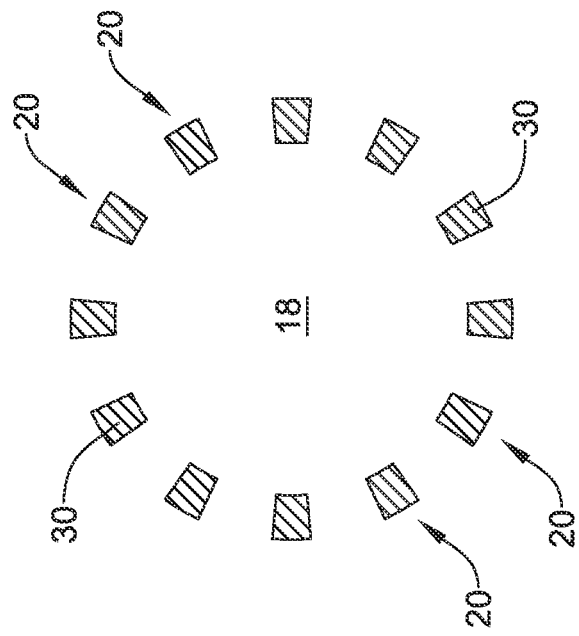
FIGS. 2A and 2B are exemplary cross-sectional views taken along lines A-A and B-B of FIG. 1, respectively, in which a proximal portion of the endoprosthesis includes a bioabsorbable material disposed on the biostable struts.
Figure 2A:
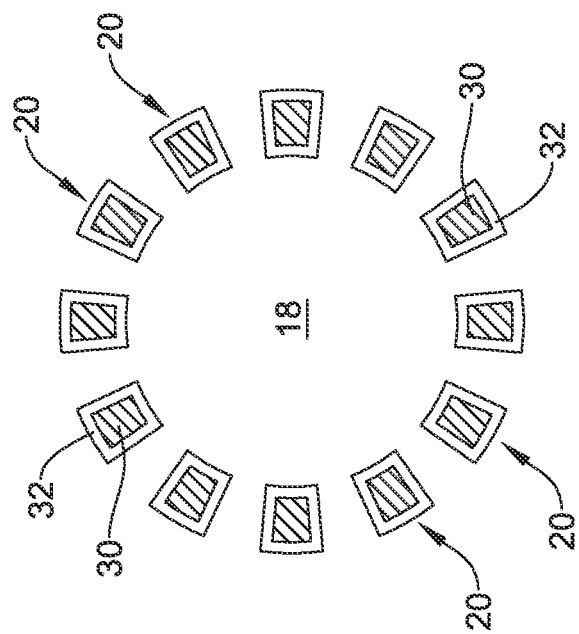

FIGS. 2A and 2B are exemplary cross-sectional views taken along the lines A-A and B-B of FIG. 1, respectively. As shown in FIG. 2A, the bioabsorbable material 32 may be disposed around the struts 20 of the proximal region 22. Hence, a layer of the bioabsorbable material 32 may surround or encapsulate the biostable material 30 of the struts 20. As shown in FIG. 2B, the distal region 24 may be devoid of the bioabsorbable material 32, thus exposing the biostable material 30. The bioabsorbable material 32 may be absorbed by the body of a patient through the blood stream, other fluids and/or other natural compositions, over a period of time after implanting the endoprosthesis 10 within the body lumen.

Figure 3B:
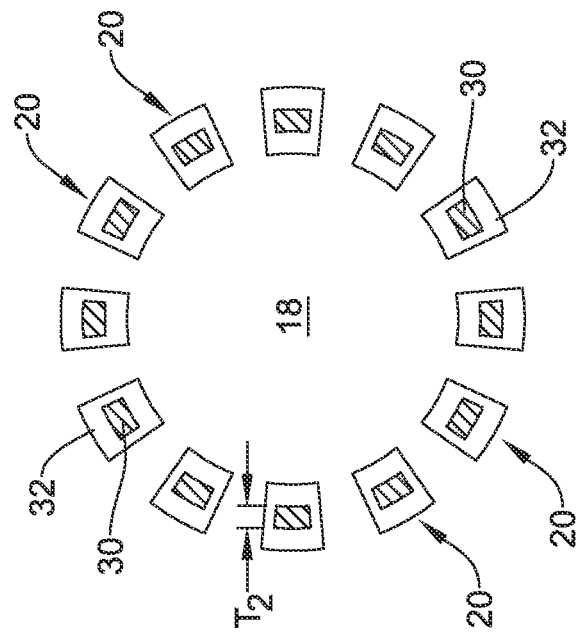
FIGS. 3A and 3B are alternative cross-sectional views taken along lines A-A and B-B of FIG. 1, respectively, in which the thickness of the proximal struts is greater than the thickness of the distal struts, and a bioabsorbable material is disposed at or on the biostable struts.
Figure 3A:
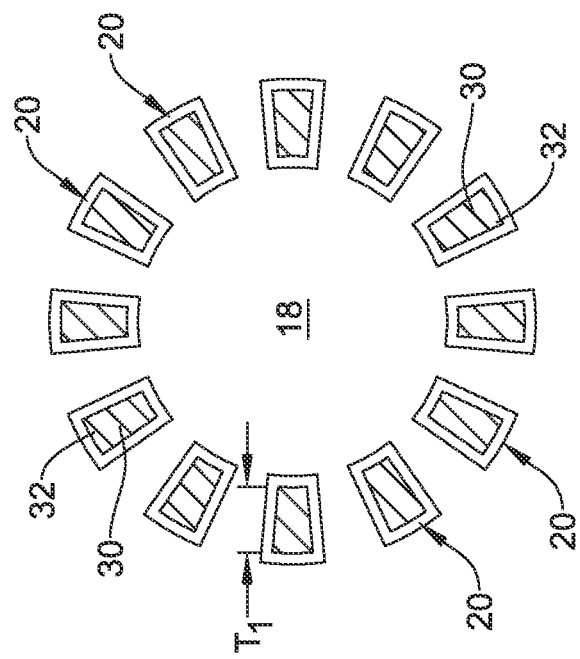

In some embodiments, for example as shown in FIGS. 3A and 3B, the thickness ($T_1$) of the biostable material 30 of the struts 20 located at the proximal region 22 may be greater than the thickness ($T_2$) of the biostable material 30 of the struts 20 located at the distal region 24. As shown in FIGS. 3A and 3B, the thickness $T_1$ of the biostable material 30 of the struts 20 in the proximal region 22 may be greater than the thickness $T_2$ of the biostable material 30 of the struts 20 of the distal region 24. Greater thickness of the struts 20 of the proximal region 22 may be provided to increase strength of the proximal region 22 as compared to the distal region 24, as required in body lumens such as the aorta ostium. A layer of the bioabsorbable material 32 may be disposed on and/or around the biostable material 30 of the struts 20 of the proximal region 22, thereby increasing the thickness and hence strength of the proximal region 22. As shown in FIG. 3B, the biostable material 30 of the struts 20 of the distal region 24 may also be coated or covered by the bioabsorbable material 32. In some instances the thickness of the bioabsorbable material 32 may be constant throughout the proximal region 22 and the distal region 24. In other instances, the thickness of the bioabsorbable material 32 throughout the proximal region 22 may be different from the thickness of the bioabsorbable material 32 throughout the distal region 24. For example, the thickness of the bioabsorbable material 32 may be greater in the distal region 24 than the proximal region 22, such that the thickness of the struts 20 may be constant throughout the length of the endoprosthesis 10. In some instances, the distal region 24 may be coated with the bioabsorbable material 32 such that there is a continuous variation in thickness from the proximal region 22 to the distal region 24.

In some embodiments, the width of the struts 20 of the proximal region 22 may be different than (e.g., greater than or less than) the width of the struts 20 in the distal region 24. FIGS. 4A and 4B are alternative cross-sectional views taken along the lines A-A and B-B of FIG. 1, respectively. In this embodiment, the width $W_1$ of the biostable material 30 of the struts 20 of the proximal region 22 may be greater than the width $W_2$ of the biostable material 30 of the struts 20 in the distal region 24, thereby increasing strength of the struts 20 of the proximal region 22. The bioabsorbable material 32 may be disposed on and/or around the biostable material 30 of the struts 20 in the proximal region 22 and/or the distal region 24. In some instances the thickness of the bioabsorbable material 32 may be constant throughout the proximal region 22 and the distal region 24. In other instances, the thickness of the bioabsorbable material 32 throughout the proximal region 22 may be different from the thickness of the bioabsorbable material 32 throughout the distal region 24. For example, the thickness of the bioabsorbable material 32 may be greater in the distal region 24 than the proximal region 22, such that the width of the struts 20 may be constant throughout the length of the endoprosthesis 10. In some instances, the interconnected struts 20 may have a continuously changing width from the proximal region 22 to the distal region 24.

In some embodiments, for example as shown in FIG. 5A, the bioabsorbable material 32 may be provided by a bioabsorbable expandable framework including a number of interconnected bioabsorbable struts 20b disposed on a biostable expandable framework including a number of interconnected biostable struts 20a in the proximal region 22. In such an embodiment, a circumferential arrangement of biostable struts 20a may be beneath a circumferential arrangement of bioabsorbable struts 20b. In other words, a bioabsorbable expandable framework of the bioabsorable material 32 may surround a biostable expandable framework of the biostable material 30 throughout the proximal region 22. The biostable struts 20a may be made from the biostable material 30 and the bioabsorbable struts 20b may be made from the bioabsorbable material 32. As shown in FIG. 5B, the distal region 24 of the expandable framework 12 may be devoid of the bioabsorbable struts 20b, and may include a circumferential arrangement of the biostable struts 20a formed of the biostable material 30. The expandable tubular framework 12 may have a first outer diameter in the proximal region 22 and a second diameter in the distal region 24.

As shown in FIGS. 5A and 5B, the outer diameter of the biostable struts 20a may be constant throughout the proximal region 22 and the distal region 24. Thus, the expandable tubular framework 12 may have a non-uniform outer diameter, with a larger outer diameter throughout the proximal region 22 due to the inclusion of the bioabsorbable struts 20b surrounding the biostable struts 20a, and a smaller outer diameter throughout the distal region 24 due to the absence of the bioabsorbable struts 20b in the distal region 24. Therefore, the expandable framework 12 may initially have a non-uniform outer diameter, however once the bioabsorbable struts 20b are absorbed, the expandable framework 12 may have a uniform outer diameter.

In alternative embodiments, such as shown in FIGS. 6A and 6B, the outer diameter of the proximal region 22 may be equal to the outer diameter of the distal region 24, so that the expandable framework 12 may initially have a constant outer diameter throughout its length i.e. from the proximal end 16 to the distal end 14. In such an embodiment, the outer diameter of the biostable struts 20a may be smaller throughout the proximal region 22 than the outer diameter of the biostable struts 20a throughout the distal region 24. For example, the biostable framework may have a necked down region between the proximal region 22 and the distal region 24 to provide the change in outer diameter. The bioabsorbable framework defined by the bioabsorbable struts 20b may surround the reduced diameter proximal region 22 of the biostable struts 20a. In some instances, the outer diameter of the bioabsorbable framework in the proximal region 22 may be approximately equal to the outer diameter of the biostable framework in the distal region 24. Thus, the expandable tubular framework 12 may have a uniform outer diameter throughout its length.

FIGS. 7A and 7B are alternative cross-sectional views taken along the lines A-A and B-B of FIG. 1. respectively. The expandable framework 12 may be made from the biostable material 30. In an embodiment, a groove or channel 34 may be disposed in a surface, such as an outer surface, of the biostable struts 30 in the proximal region 22 of the expandable framework 12. The bioabsorbable material 32 may be disposed in the grooves or channels 34 of the biostable struts 30 in the proximal region 22 to increase the initial strength of the proximal region 22. However, the distal region 24, which may or may not include the grooves or channels 34 in the biostable struts 30, may be devoid of the bioabsorbable material 32, or may include a lesser amount of the bioabsorbable material 32. Over a period of time as the bioabsorbable material 32 is absorbed by the body, the strength of the proximal region 22 may be reduced from the initial strength of the proximal region 22.

FIG. 8 is a cross-sectional view illustrating placement of an exemplary endoprosthesis at an aorta ostium 86. In the cardiovascular system, the aorta 84 branches into a coronary vessel 82 at a branch point referred to as the aorta ostium 86. The vessel 82 includes a vessel lumen 80, into which the endoprosthesis 10 may be implanted. One of the endoprostheses discussed above may be positioned in the vessel lumen 80 with the proximal region 22 of the endoprosthesis 10 proximate the aorta ostium 86 and the distal region 24 of the endoprosthesis extending into the vessel lumen 80 distal of the aorta ostium 86. Thus, the proximal region 22, which may have an initial strength greater than the initial strength of the distal region 24 may facilitate retention of the endoprosthesis 10 proximate the aorta ostium 86. The strength of the proximal region 22 may decrease over a period of time as the bioabsorbable material is absorbed by the patient, thus the strength of the proximal region 22 may be less than the initial strength of the proximal region 22.

FIG. 8 illustrates another embodiment of the endoprosthesis 10 in which the endoprosthesis 10 may include a number of interconnected struts 20 made from the biostable material 30 and a layer of the bioabsorbable material 32 may be disposed on the biostable struts 20. In the embodiment shown in FIG. 8, the thickness of the biostable material 30 of the struts 20 may vary along the length of the endoprosthesis 10. For instance, the thickness of the biostable material 30 of the struts 20 may vary continuously along the length of the endoprosthesis 10, endoprosthesis 10 may include one or more stepped transitions in the thickness of the biostable material 30 of the struts 20 at different locations along the length of the endoprosthesis 10, or the thickness of the biostable material 30 may change in another fashion. In some instances, the thickness of the biostable material 30 of the struts 20 in the distal region of the endoprosthesis 10 may be in a range of about 0.001 inches to about 0.002 inches, and the thickness of the biostable material 30 of the struts 20 in the proximal region of the endoprosthesis 10 may be in a range of about 0.003 inches to about 0.004 inches. In some instances, the thickness of the struts 20 in a middle region, intermediate the distal region and the proximal region of the endoprosthesis 10, may be in a range of about 0.002 inches to about 0.003 inches, for example. Accordingly, the thickness of the struts 20 in the proximal region of the endoprosthesis 10 may be greater as compared to the thickness of the struts 20 in the middle and distal regions of the endoprosthesis 10, thereby providing more strength to the struts 20 located in the proximal region of the endoprosthesis 10. Also, the biostable material 30 may act as a scaffold to avoid or prevent the bioabsorbable material 32 from disengaging and drifting towards the main aortic vessels.

In some instances, the ratio of the biostable material 30 to the bioabsorbable material 32 may be 1:1. In other instances, the ratio of the biostable material 30 to the bioabsorbable material 32 may be 1:2, 1:3, 2:3, or 1:4 for example. In some embodiments, the ratio of the biostable material 30 to the bioabsorbable material 32 may increase or decrease along the length of the endoprosthesis 10. For example, in some instances, the ratio of the biostable material 30 to the bioabsorbable material 32 may change (e.g., increase or decrease) continuously along the length of the endoprosthesis 10 or may include one or more stepped transitions along the length of the endoprosthesis 10.

In some instances, the thickness of the biostable material 30, the bioabsorbable material 32, and/or the total thickness of the struts 20, may decrease from the proximal end to the distal end of the endoprosthesis 10. In one embodiment, as shown with the alternative cross-sections shown in FIG. 8A, corresponding to the cross-sections shown in FIG. 8, the thickness of the bioabsorbable material 32 may increase from the proximal end to the distal end of the endoprosthesis 10, as the thickness of the biostable material 30 decreases from the proximal end to the distal end of the endoprosthesis 10, or the thickness of the bioabsorbable material 32 may increase from the proximal end to the distal end of the endoprosthesis 10, as the thickness of the biostable material 30 remains constant. In other instances, the thickness of the bioabsorable material 32 may decrease from the proximal end to the distal end of the endoprosthesis 10, as the biostable material 30 decreases or remains constant. The total thickness of the struts 20, may increase, decrease, or remain constant from the proximal end to the distal end as the ratio of the biostable material 30 to the bioabsorbable material 32 changes (e.g., increases or decreases) along the length of the endoprosthesis 10.

In some instances, the thickness of the biostable material 30, the bioabsorbable material 32, and/or the total thickness of the struts 20, may decrease from the proximal end, the distal end, or the proximal and distal ends of the endoprosthesis 10 to a region between the proximal and distal ends of the endoprosthesis 10. The thickness of the biostable material 30, the bioabsorbable material 32, and/or the total thickness of the struts 20 may likewise increase from the proximal end, the distal end, or the proximal and distal ends of the endoprosthesis 10 to a region between the proximal and distal ends of the endoprosthesis 10. In some instances, the thickness of the biostable material 30, the bioabsorbable material 32, and/or the total thickness of the struts 20, may increase or decrease along one or more regions along the longitudinal axis of endoprosthesis 10.

Figure 9:
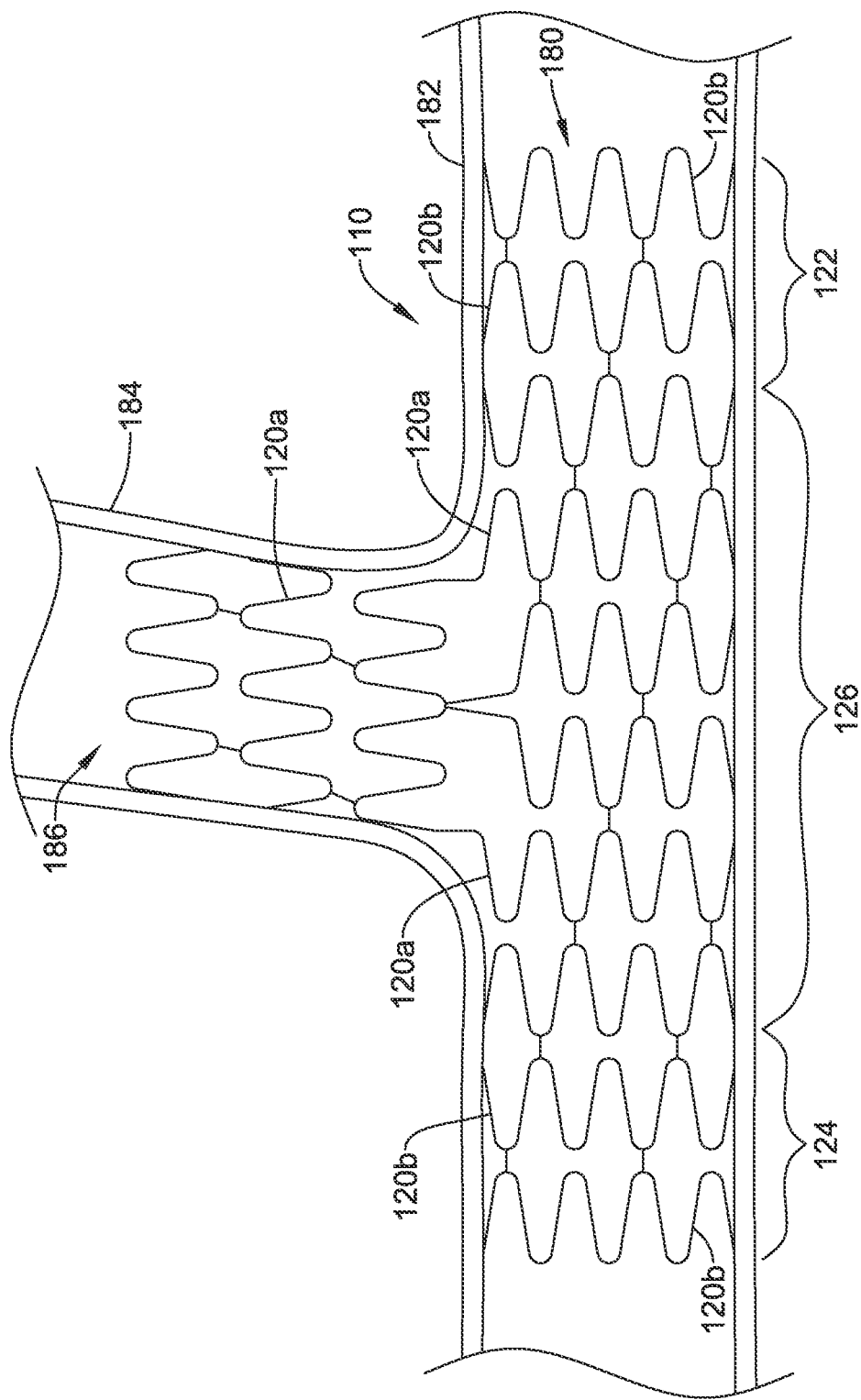
FIG. 9 is a cross-sectional view illustrating placement of an exemplary endoprosthesis in a bifurcated vessel.

FIG. 9 is a cross-sectional view illustrating placement of an exemplary endoprosthesis in a bifurcated vessel. The vessel 182 has a vessel lumen 180 and bifurcates into a branch vessel 184. The branch vessel 184 includes a lumen 186. An endoprosthesis, such as a stent 110, may be implanted with a portion in each of the lumens 180, 186. The stent 110 may include a number of interconnected struts. The stent 110 can be implanted in the bifurcated vessel 182 and may include a bioabsorbable proximal segment 124 and a bioabsorbable distal segment 122, with a biostable segment 126 located between the bioabsorbable proximal segment 124 and the bioabsorbable distal segment 122. Each of the bioabsorbable segments 124, 122 may include a number of interconnected bioabsorbable struts 120*b*. The biostable segment 126 may include a number of interconnected biostable struts 120*a*. At least a portion of the biostable struts 120*a* of the intermediate segment 126 may extend into the vessel lumen 186 of the branch vessel 184 to provide support at the bifurcation. The biostable struts 120*a* may be implanted in the branch vessel 184 so that the biostable struts 120*a* extending into the branch vessel 184 may remain intact after the bioabsorbable struts 120*b* have been absorbed by the body. In some embodiments, the stent 110 may be a branched stent such that a portion of the stent 110 extends to form a branched portion and a central axis of the branched portion is substantially perpendicular or oblique to a longitudinal axis of a main portion of the stent 110.

Further, the bioabsorbable struts 120*b* may be provided on either side of the biostable struts 120*a* in the vessel 182 to provide initial structural support of the stent 110 in the vessel 182. Over a period of time, the struts 120*b* may get absorbed in the vessel 182, leaving the biostable struts 120*a* in place.

Figure 10:
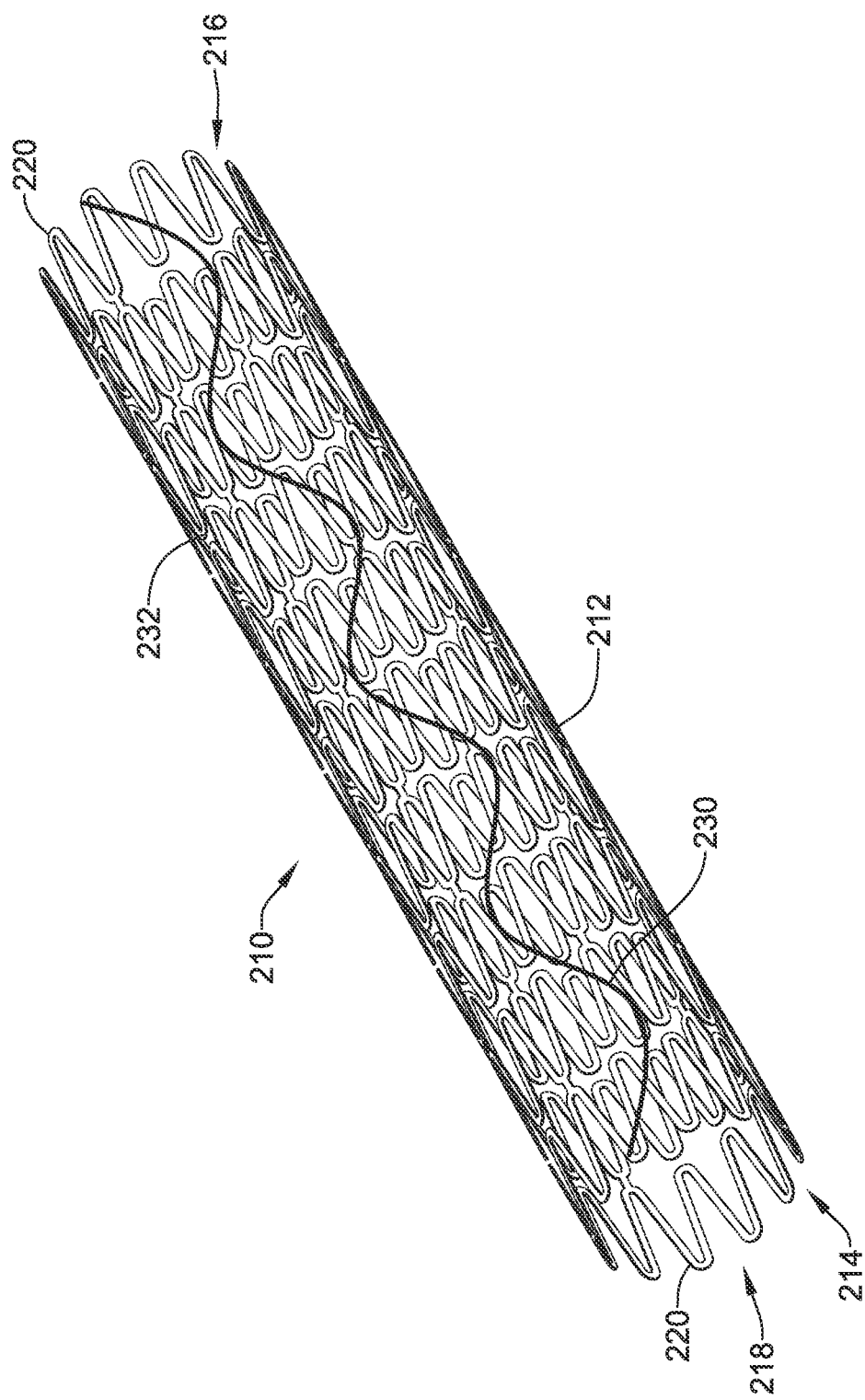
FIG. 10 is a perspective view of an alternative endoprosthesis including a biostable wire.

FIG. 10 is a top view of an alternative endoprosthesis including a biostable wire disposed along a portion of the length of the endoprosthesis. As shown in FIG. 10, the endoprosthesis may include a stent 210. The stent 210 may include an expandable tubular framework 212 having a proximal end 216, a distal end 214, and a number of interconnected struts 220 disposed about a longitudinal axis of the stent 210 that defines a lumen 218 therethrough. The struts 220 may form a mesh-like framework 212 as shown in FIG. 10. The struts 220 may be formed from a bioabsorable material to form bioabsorbable struts 232. The bioabsorbable struts 232 may be capable of being absorbed in the body lumen after being implanted in the body lumen over a period of time. In some embodiments, a biostable wire 230, or a plurality of biostable wires 230, may be positioned along (e.g., laid over, interweaved with, laid under, etc.) the expandable framework 212 to provide structural support to the stent 210. The biostable wire 230 may remain in the body lumen permanently even after the expandable framework 212 has been absorbed in the body lumen.

In some instances, the elongate biostable wire(s) 230 may extend generally longitudinal along the expandable framework 212. In embodiments having a plurality of biostable wires 230, the biostable wires 230 may be arranged uniformly or non-uniformly around the circumference of the expandable framework 212. In some instances, the longitudinally extending wire(s) 230 may be substantially straight, while in other instances the longitudinally extending wire(s) 230 may follow an undulating, a curved, a helical, or other desired path.

Figure 11A:
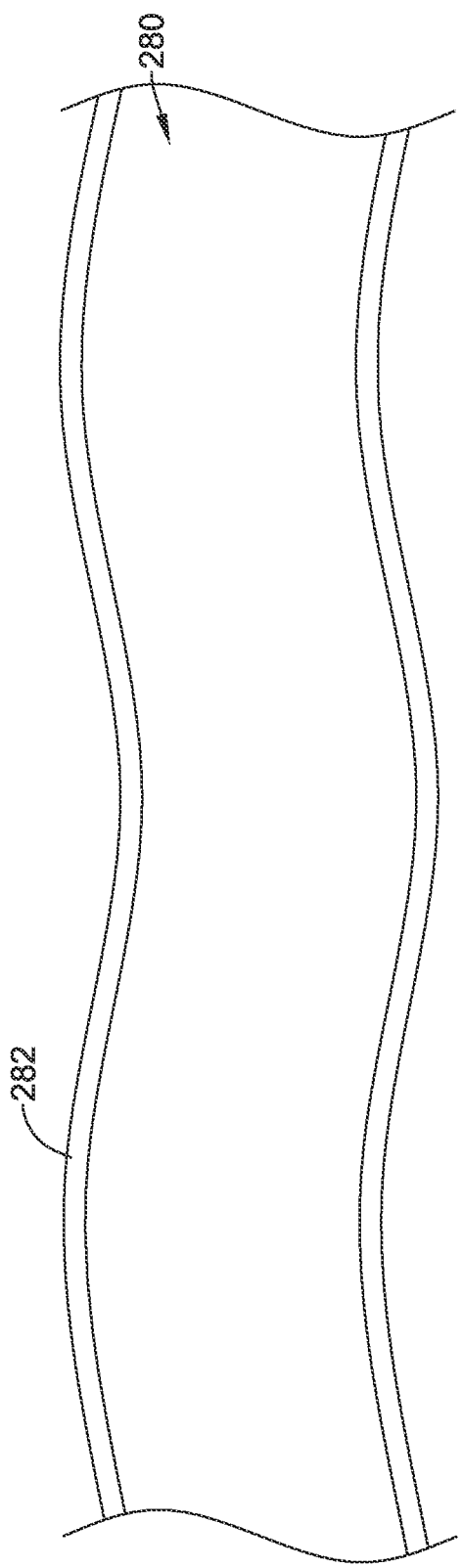
FIGS. 11A-11C illustrate aspects of using the endoprosthesis of FIG. 10 in a vessel.
Figure 11B:
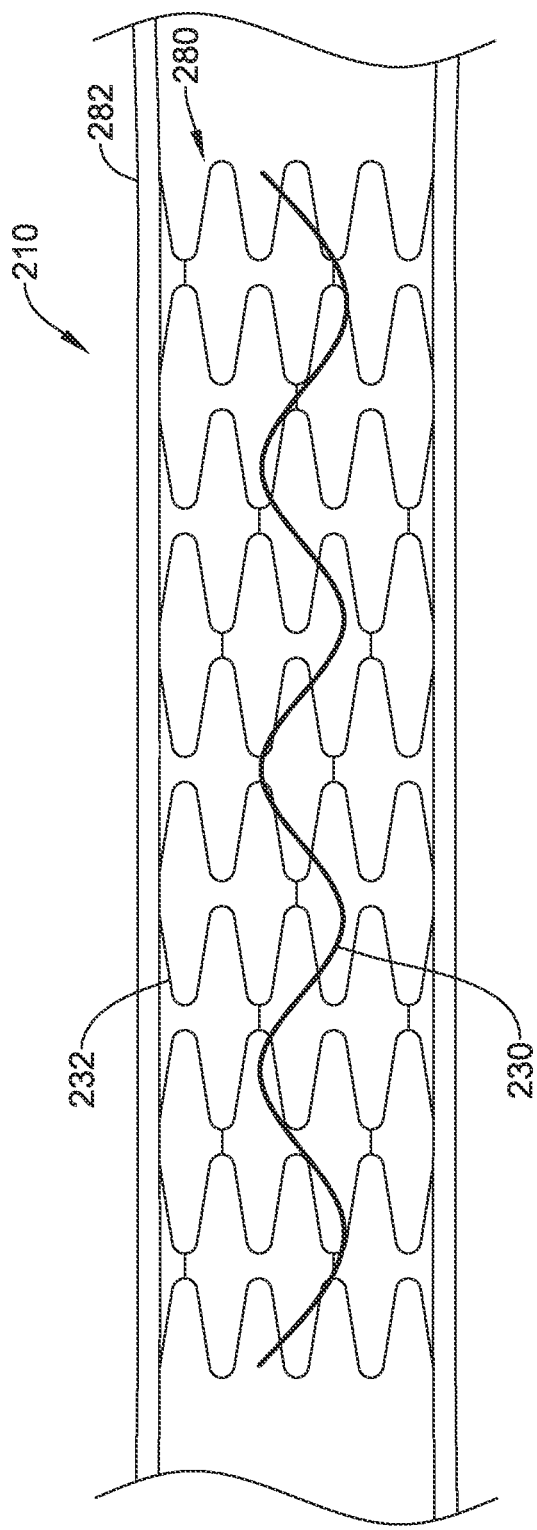
Figure 11C:
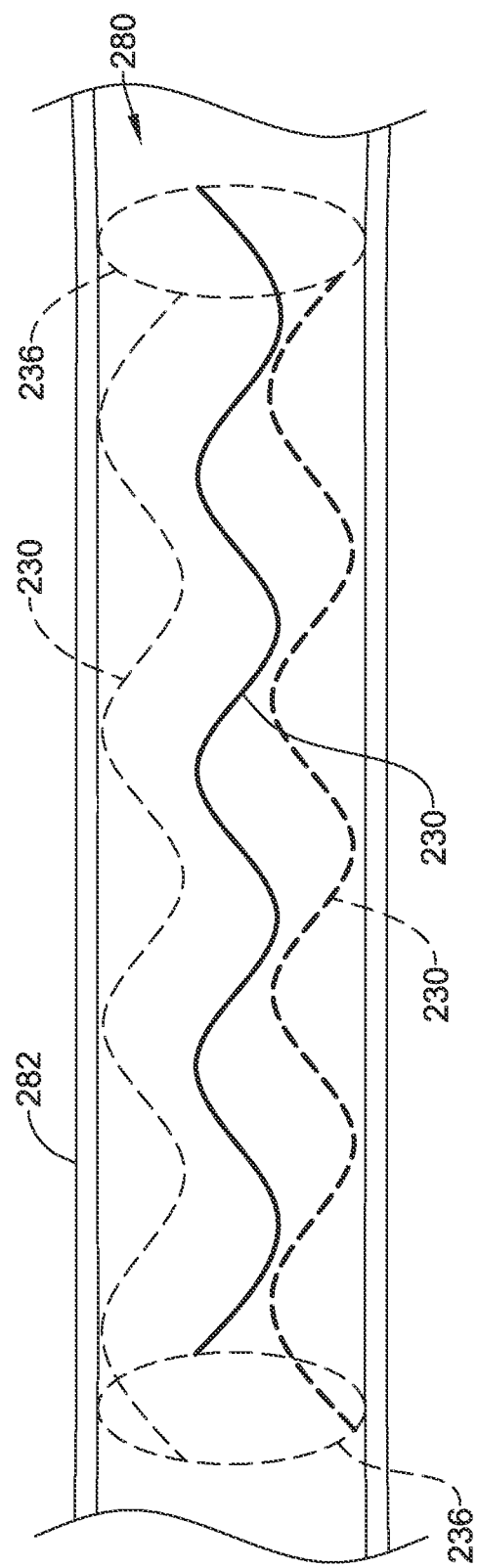

Various aspects of implanting the stent 210 in a vessel 282 within the body of a patient are shown in FIGS. 11A-11C. As shown in FIG. 11A, the vessel 282, which may follow a tortuous pathway in some instances, may include a vessel lumen 280. The vessel 282 may be stenosed, weakened, or otherwise require intervention with the stent 210. In some cases, the vessel 282 may be weakened by aneurysm. Accordingly, the stent 210 may be implanted within the vessel lumen 280 of the vessel 282, as shown in FIG. 11B. Different features have already been explained in FIG. 10, such as the biostable wire 230 and the bioabsorbable struts 232. In some embodiments, a number of the biostable wires 230 may be positioned along the bioabsorbable struts 232. At some time after implantation, for example 2 years or more, the bioabsorbable struts 232 may be fully absorbed in the vessel 282. However, the biostable wire(s) 230 may remain in the vessel lumen 280 even after absorption of the bioabsorbable struts 232 by the body of the patient, as shown in FIG. 11C. The presence of the biostable wire(s) 230 may facilitate restoring vasomotion and strength of the vessel 282, and may not interfere with radial compression/dilation of the vessel 282 after the bioabsorbable struts 232 have been fully absorbed. Additionally or alternatively, the biostable wire(s) 230 may serve as a permanent re-shaping scaffold, reducing or otherwise modifying the curvature of the vessel 282 even after absorption of the bioabsorbable struts 232. For example, the biostable wire(s) 230 may provide a degree of straightening of the vessel 282, thus making the vessel 282 less tortuous, through the permanent presence of the biostable wire(s) 230 after the bioabsorbable struts 232 have been absorbed and vasomotion has been restored.

In some embodiments, the stent 210 may include a plurality of biostable wires 230, and one or more biostable rings, such as a biostable ring 236 disposed on either side of the biostable wires 230 proximate the ends of the stent 210. The ring 236 may be provided to give a structural support to the biostable wires 230 and to remain the biostable wires 230 intact in the vessel lumen 280 after the bioabsorbable struts 232 have been fully absorbed. The diameter of the ring 236 may be such that the ring 236 fits into the vessel lumen 280. In some instances, the ring 236 may be expanded in the vessel lumen 280 upon implantation of the stent 210. In such an embodiment, over a period of time, along with the biostable wires 230, the rings 236 may also remain in the vessel lumen 280 to retain the biostable wires 230. The biostable wires 230 and the rings 236 may facilitate restoring vasomotion and strength of the vessel 282, and may not interfere with radial compression/dilation of the vessel 282.

Figure 12B:
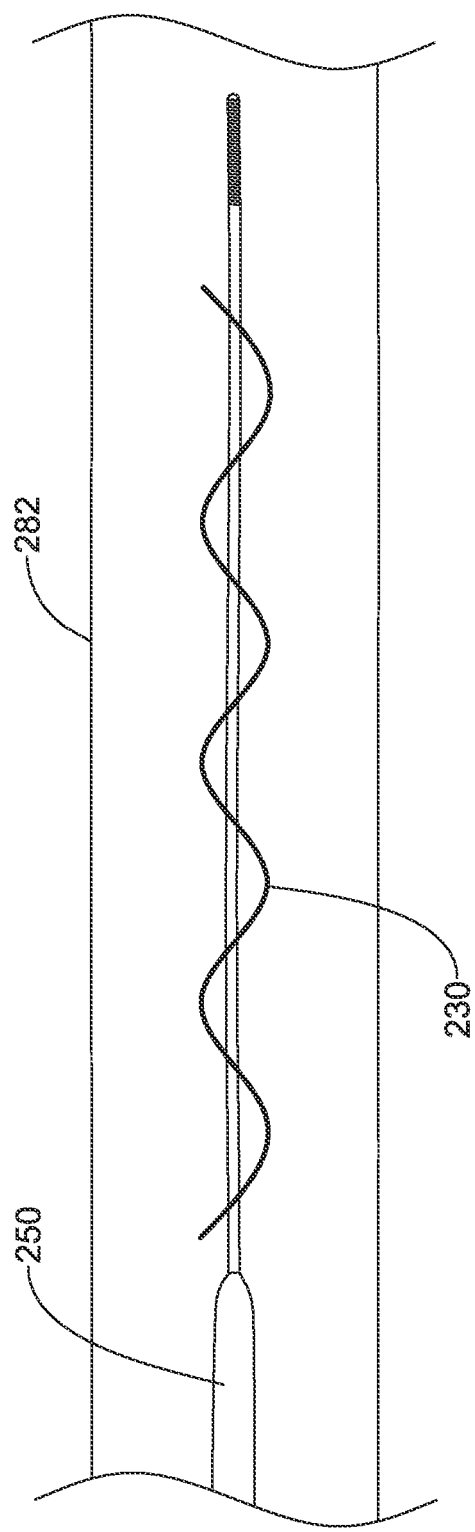

FIGS. 12A and 12B are schematics that illustrate some advantages of the biostable wire 230 of the endoprosthesis of FIG. 10. As shown in FIG. 12A, the vessel 282 may include the vessel lumen 280. At some time after implantation of the stent 210, the vessel lumen 280 may become occluded by an occlusion 290 in the region of the stent 210. As discussed above, the biostable wire 230 may remain in the vessel 282 after the bioabsorbable struts 232 have been absorbed by the body and thus may extend through a region including the occlusion 290. In the case of restenosis, for example, there may be a situation when recanalization of the vessel 282 past the occlusion 290 and the biostable wire 230 may be desired. For example, in instances in which the occlusion 290 is a chronic total occlusion (CTO) or otherwise substantially occludes the lumen 280, it may be impossible or impracticable to pass a recanalization device through the occlusion 290. In such instances, recanalization of the vessel 282 via a subintimal pathway may be achieved with a medical device 250, for example.

The biostable wire 230, which may be visible using fluoroscopy, may facilitate guiding the medical device 250 through the subintimal pathway. For example, the biostable wire 230 may provide a visual indication of the extent of the occlusion 290 such that the physician may navigate the medical device 250 across the occlusion 290.

FIG. 12B is a top view of the biostable wire 230 in the vessel 282 and the medical device 250 introduced for subinitimal access across the occlusion 290. As discussed above, the biostable wire 230 may be visible using fluoroscopy to facilitate guiding the medical device 250 through the subintimal pathway. Once the physician confirms that the distal end of the medical device 250 has passed distal of the occlusion 290, reentry into the true lumen distal of the occlusion 290 may be achieved with the medical device 250, or other medical device.

A method of implanting an endoprosthesis, such as an endoprosthesis described above, in a coronary artery proximate an aortic ostium may include a number of consecutive, non-consecutive, simultaneous, non-simultaneous, or alternative steps. The method may also include providing the endoprosthesis. The endoprosthesis may be implanted in the coronary artery with the proximal end proximate to the aorta ostium. The expandable framework may expand to exert a radially outward force against the coronary artery. The proximal region of the endoprosthesis proximate to the proximal end may have an initial stiffness when expanded. The initial stiffness of the proximal region may be greater than an initial stiffness of the distal region. The stiffness of the proximal region may be reduced to a greater extent as compared to that of the distal region over a period of time as the bioabsorbable material is absorbed.

It should be understood that this disclosure is, in many respects, only illustrative. Changes may be made in details, particularly in matters of shape, size, and arrangement of steps, without exceeding the scope of the disclosure. This may include, to the extent that it is appropriate, the use of any of the features of one exemplary embodiment in other embodiments. The disclosure's scope is, of course, defined in the language in which the appended claims are expressed.

What is claimed is:

1. An endoprosthesis comprising:
   an expandable tubular framework having a proximal end, a distal end, and a lumen extending therethrough, the expandable tubular framework including a plurality of interconnected biostable struts;
   the expandable tubular framework having a proximal region extending distally from the proximal end to an intermediate location and a distal region extending proximally from the distal end to the intermediate location;
   wherein the distal region of the expandable tubular framework is more flexible than the proximal region;
   wherein the proximal region of the expandable tubular framework includes a bioabsorbable material disposed on the interconnected biostable struts and the distal region of the expandable tubular framework is devoid of a bioabsorbable material;
   wherein the proximal region of the expandable tubular framework includes a bioabsorbable tubular structure disposed around the interconnected biostable struts and the distal region of the expandable tubular framework is devoid of the bioabsorbable tubular structure; and
   wherein the expandable tubular framework has a first outer diameter in the proximal region and a second diameter in the distal region, the first diameter being less than the second diameter.

2. The endoprosthesis of claim 1, wherein the bioabsorbable tubular structure has an outer diameter approximately equal to the second diameter.

3. An endoprosthesis comprising:
   an expandable tubular framework having a proximal end, a distal end, and a lumen extending therethrough, the expandable tubular framework including a plurality of interconnected biostable struts;
   the expandable tubular framework having a proximal region extending distally from the proximal end to an intermediate location and a distal region extending proximally from the distal end to the intermediate location;
   wherein the distal region of the expandable tubular framework is more flexible than the proximal region;
   wherein the proximal region of the expandable tubular framework includes a bioabsorbable material disposed on the interconnected biostable struts and the distal region of the expandable tubular framework is devoid of a bioabsorbable material; and
   wherein the proximal region of the expandable tubular framework includes a bioabsorbable material disposed in a groove formed in the interconnected biostable struts and the distal region of the expandable tubular framework is devoid of the bioabsorbable material.

4. An endoprosthesis comprising:
   an expandable tubular framework having a proximal end, a distal end, and a lumen extending therethrough, the expandable tubular framework including a plurality of interconnected biostable struts;
   the expandable tubular framework having a proximal region extending distally from the proximal end to an intermediate location and a distal region extending proximally from the distal end to the intermediate location;
   wherein the distal region of the expandable tubular framework is more flexible than the proximal region;
   wherein the proximal region of the expandable tubular framework includes a bioabsorbable material disposed on the interconnected biostable struts and the distal region of the expandable tubular framework is devoid of a bioabsorbable material; and
   wherein the interconnected biostable struts have a first thickness in the proximal region and the interconnected biostable struts have a second thickness in the distal region, wherein the first thickness is greater than the second thickness.

5. The endoprosthesis of claim 4, wherein the proximal region of the expandable tubular framework includes a bioabsorbable material disposed on the interconnected biostable struts.

6. An endoprosthesis comprising:
   an expandable tubular framework having a proximal end, a distal end, and a lumen extending therethrough, the expandable tubular framework including a plurality of interconnected biostable struts;
   the expandable tubular framework having a proximal region extending distally from the proximal end to an intermediate location and a distal region extending proximally from the distal end to the intermediate location;
   wherein the distal region of the expandable tubular framework is more flexible than the proximal region;
   wherein the proximal region of the expandable tubular framework includes a bioabsorbable material disposed on the interconnected biostable struts and the distal region of the expandable tubular framework is devoid of a bioabsorbable material; and
   wherein the interconnected biostable struts have a first width in the proximal region and the interconnected biostable struts have a second width in the distal region, wherein the first width is greater than the second width.

7. The endoprosthesis of claim 6, wherein the proximal region of the expandable tubular framework includes a bioabsorbable material disposed on the interconnected biostable struts.

8. An endoprosthesis comprising:
   an expandable tubular framework having a proximal end, a distal end, and a lumen extending therethrough, the expandable tubular framework including a plurality of interconnected biostable struts;
   the expandable tubular framework having a proximal region extending distally from the proximal end to an intermediate location and a distal region extending proximally from the distal end to the intermediate location;

wherein the distal region of the expandable tubular framework is more flexible than the proximal region;

wherein the proximal region of the expandable tubular framework includes a bioabsorbable material disposed on the interconnected biostable struts and the distal region of the expandable tubular framework is devoid of a bioabsorbable material; and wherein the interconnected biostable struts have a continuously changing thickness from the proximal region to the distal region, wherein a thickness of the interconnected biostable struts at the proximal end of the expandable tubular framework is greater than a thickness of the interconnected biostable struts at a distal end of the expandable tubular framework.

9. An endoprosthesis comprising:

an expandable tubular framework having a first end, a second end, and a lumen extending therethrough, the expandable tubular framework including a plurality of interconnected bioabsorbable struts;

at least one biostable wire extending generally longitudinally along the expandable tubular framework;

wherein at least one biostable wire is configured to provide longitudinal support to a vessel wall after the expandable tubular framework is absorbed.

10. The endoprosthesis of claim 9, wherein the at least one biostable wire includes a plurality of biostable wires circumferentially arranged around a circumference of the expandable tubular framework.

11. The endoprosthesis of claim 10, further comprising a biostable ring attached to the plurality of biostable wires.

12. The endoprosthesis of claim 10, wherein a first end of the plurality of biostable wires is attached to a first biostable ring and a second end of the plurality of biostable wires is attached to a second biostable ring.

13. A method of implanting an endoprosthesis in a coronary artery proximate an aortic ostium, the method comprising:

positioning the endoprosthesis in the coronary artery with a proximal end of the endoprosthesis proximate the aortic ostium, the endoprosthesis including an expandable tubular framework and having a lumen extending therethrough from the proximal end to a distal end, the expandable tubular framework including a plurality of interconnected biostable struts and a bioabsorbable material disposed on at least a portion of the interconnected biostable struts; and expanding the expandable tubular framework to exert a radially outward force against the coronary artery;

wherein a proximal region of the endoprosthesis proximate the proximal end has an initial stiffness when expanded greater than an initial stiffness of a distal region of the endoprosthesis; and wherein the proximal region is configured to have a reduced stiffness less than the initial stiffness over a period of time as the bioabsorbable material is absorbed.

14. The method of claim 13, wherein the stiffness of the proximal region is reduced at a greater rate than the stiffness of the distal region over the period of time.

15. The method of claim 13, wherein the proximal region of the expandable tubular framework includes the bioabsorbable material and the distal region of the expandable tubular framework is devoid of a bioabsorbable material, wherein the bioabsorbable material is absorbed over a period of time to reduce the difference in stiffness of the proximal portion relative to the stiffness of the distal portion.

16. The method of claim 13, wherein the bioabsorbable material is disposed in a groove formed in the interconnected biostable struts in the proximal region.

17. The method of claim 13, wherein the interconnected biostable struts have a continuously changing thickness from the proximal region to the distal region, wherein a thickness of the interconnected biostable struts at the proximal end of the expandable tubular framework is greater than a thickness of the interconnected biostable struts at a distal end of the expandable tubular framework.

* * * * *